United States Patent [19]

Walsh et al.

[11] 3,970,729
[45] July 20, 1976

[54] PROCESS OF SYNTHESIZING DI-POLYOXYLALKYLENE HYDROXYMETHYLPHOSPHONATE

[75] Inventors: Edward N. Walsh, New City; Kyung Sup Shim, Irvington, both of N.Y.

[73] Assignee: Stauffer Chemical Company, Westport, Conn.

[22] Filed: Aug. 5, 1974

[21] Appl. No.: 494,685

[52] U.S. Cl. .......................... 260/978; 260/30.6 R; 260/45.7 P; 260/502.4 R; 260/970
[51] Int. Cl.² .................. C07F 9/40; C08F 2/44
[58] Field of Search ................. 260/978, 970, 502.4

[56] References Cited
UNITED STATES PATENTS

| | | | |
|---|---|---|---|
| 2,579,810 | 12/1951 | Fields | 260/970 |
| 3,294,710 | 12/1966 | Rosenberg et al. | 260/970 UX |

OTHER PUBLICATIONS

Van Wazer "Phosphorus and its Compounds," vol. 1, p. 371, (1958), Interscience Publishers Inc., New York.

*Primary Examiner*—Anton H. Sutto
*Attorney, Agent, or Firm*—William R. Robinson

[57] ABSTRACT

Di-polyoxyalkylene hydroxymethylphosphonate is prepared by contacting phosphorous acid and formaldehyde, or a formaldehyde polymer such as trioxane or paraformaldehyde, preferably in an aqueous medium, to yield a hydroxymethylphosphonic acid intermediate. The intermediate is then contacted wiyth an alkylene oxide selected from ethylene oxide, propylene oxide or butylene oxide to yield di-polyoxyalkylene hydroxymethylphosphonate having the structureal formula:

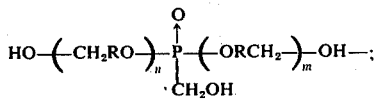

wherein R is $CH_2$,

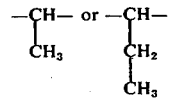

$n + m = 2 - 10$. Di-polyoxyalklene hydroxymethylphosphonate is utilized as a flame retardant, a stabilizer for polyester film and as a plasticizer for cellulose acetate and polyvinyl acetate, among others.

7 Claims, No Drawings

PROCESS OF SYNTHESIZING DI-POLYOXYLALKYLENE HYDROXYMETHYLPHOSPHONATE

BACKGROUND OF THE INVENTION

1. Field of the Invention

The present invention relates to a new and improved process for the preparation of di-polyoxyalkylene hydroxymethylphosphonate.

2. The Prior Art

Di-polyoxyethylene hydroxymethylphosphonate has been prepared by first reacting phosphorus trichloride with formaldehyde. This reaction is followed by hydrolysis to yield hydroxymethyl phosphonic acid and residual chlorine. (See: M. I. Kabachnik and E. S. Shepeleva; Izvest. Akad. Nauk-SSSR, p. 185 (1951). The hydroxymethyl phosphonic acid then is reacted with excess ethylene oxide to produce di-polyoxyethylene hydroxymethylphosphonate.

A side product of the prior art process is bis-chloromethylether, a known carcinogen. (See Federal Register, Volume 39, Number 20, Jan. 29, 1974, page 3757.)

SUMMARY OF THE INVENTION

In accordance with the present invention, there is provided a new method for preparing compounds of the formula:

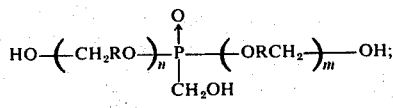

wherein R is $CH_2$,

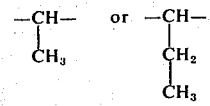

$n + m = 2-10$. The method comprises contacting the reactants phosphorous acid and formaldehyde or a formaldehyde polymer such as trioxane or paraformaldehyde, preferably in an aqueous solution, to form an intermediate compound having the structural formula:

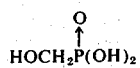

The intermediate compound is then contacted preferably with ethylene oxide, propylene oxide or butylene oxide also can be used, to provide the di-polyoxyalkylene hydroxymethylphosphonate of Formula I. Bis-chloromethyl ether is not formed in the method of the present invention and there is no residual chlorine.

The following equations (1) and (2) are believed representative of the reaction by which the intermediate is formed and the reaction by which the di-polyoxyalkylene hydroxymethylphosphonate is formed, respectively.

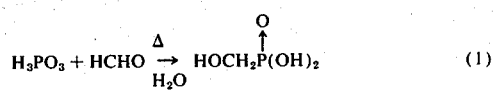

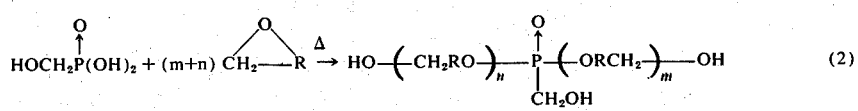

wherein R and $n + m$ are as defined above.

Reactants utilized in the process of the present invention can be employed in stoichiometric amounts, although an excess of any reactant can be used if desired.

In preparing the intermediate, phosphorous acid and formaldehyde or a formaldehyde polymer such as trioxane or paraformaldehyde are contacted alone or, preferably, in an aqueous medium at a temperature between about 90°C. and about 150°C. The preferred temperature is between about 100°C. and about 135°C.

Reaction times can vary over a wide range without adversely affecting the process. The optimum reaction times can easily be determined by one skilled in the art. Reaction times are dependent on the reaction temperature, the amount of formaldehyde and the quantity of water present in the reaction mixture. An increase in reaction temperature or the amount of formaldehyde will decrease reaction time. Reaction time is increased with increases in the quantity of water present. The reaction is usually complete in about 1 to 10 hours. After the reaction, the volatile components are usually separated from the hydroxymethyl phosphonic acid intermediate by conventional procedures.

Production of the intermediate compound according to reaction (1) can conveniently be effected by introducing the individual reactants, phosphorous acid and formaldehyde in water, into a heated reaction zone equipped with a stirring or mixing means. The reactants can also be mixed before entering the reaction zone. An enclosed reaction zone opening to a condenser can be conveniently utilized. The reaction zone is provided with suitable means to monitor temperature. The mixture is heated to a temperature between about 90°C. and about 150°C. and the intermediate compound is formed. Phosphite content can be continuously monitored by, for example, gravimetric phosphorus analysis of samples taken from the mixture.

The intermediate compound is purified by stripping off the water and unreacted formaldehyde under a reduced pressure between about 10 mm Hg. and about 760 mm Hg. absolute at a temperature between about 50°C. and about 120°C.

The identification of the intermediate can be achieved by infra-red analysis, nuclear magnetic resonance spectra or gravimetric or volumetric phosphorus analysis.

The yield of the intermediate is generally about 95 to 100% of theoretical.

Di-polyoxyalkylene hydroxymethylphosphonate is formed by contacting the hydroxymethyl phosphonic acid intermediate with an alkylene oxide, preferably ethylene oxide, or with propylene oxide or butylene oxide, at a temperature between about 30° and about 100°C. Reaction time can vary over a wide range without adversely affecting the process. The optimum reaction time can easily be determined by one skilled in the art. Reaction times can be decreased by increasing the reaction temperature or rate of alkylene oxide addition. Reaction times between about 5 to about 50 hours are typical.

Reaction of the hydroxymethyl phosphonic acid with alkylene oxide according to reaction (2) can conveniently be effected by rapidly agitating the molten intermediate compound while adding alkylene oxide gas. Temperature in the reaction zone is maintained between about 30°C. and 100°C. during the reaction. Alkylene oxide is introduced into the reaction mixture until the acid number of the reaction mixture is about zero.

A glass lined reaction zone is preferred to avoid color problems that may occur with metal reaction zones. Iron, for example, causes an undesired yellow color in the di-polyoxyalkylene hydroxymethylphosphonates produced.

The di-polyoxyalkylene hydroxymethylphosphonate composition is purified by conventional methods such as stripping off the volatile components from the reaction mixture at an elevated temperature under reduced pressure, by contact with an inert gas, or by other means known in the art for separating materials having different boiling points. It is preferred to remove the volatile components at a temperature of from about 25°C. to about 120°C. under reduced pressure. Preferred temperatures are between about 50°C. and about 100°C. Suitable pressures are between about 10 mm Hg. and 760 mm Hg. absolute.

The identification of the final products can be achieved by phosphite analysis, volumetric or gravimetric phosphorus analysis, infra-red analysis, nuclear magnetic resonance spectra, acidity determination or other conventional procedures.

The di-polyoxyalkylene hydroxymethylphosphonate composition produced in accordance with the present invention can be used as a stabilizer for polyester film or as a plasticizer for cellulose acetate, polyvinyl acetate or the like. The composition is also used as a flame retardant for thermoset resins such as urethanes, cross-linked polyester resins and aminoplasts, and for thermoplastic resins such as acrylates and polyester fibers. The composition is also useful as a lubricant and a hydraulic fluid.

The following examples are submitted to illustrate but not to limit the present invention.

EXAMPLE 1

Preparation of Hydroxymethyl Phosphonic Acid

In a 1 liter round bottom flask equipped with a mechanical stirrer was placed 500 grams (6.25 mole) phosphorous acid, 275 grams (9.17 mole) paraformaldehyde and 50 grams distilled water. The mixture was heated at 115°–125°C. with stirring for a period of 9 hours. The volatile components were then separated from the reaction mixture by heating the mixture at 120°C. under 60–70 mm Hg. absolute pressure for 3 hours and then at 120°C. under 15 mm Hg. absolute for an additional 3 hours. There was obtained 727 grams of a colorless liquid which solidified at room temperature.

Analysis showed a phosphorus content equal to 28.3% and a phosphite content of 0.26%.

EXAMPLE 2

Preparation of Di-polyoxyethylene Hydroxymethylphosphonate

In a 500 ml. round bottom flask, was placed 150 grams of the product of Example 1. The flask was heated to 65°C. Ethylene oxide was introduced into the liquid through a gas dispersing tube while maintaining the reaction temperature at 65°–70°C. A 400 gram quantity of ethylene oxide was added to the flask over a period of 40 hours. The acid number of the reaction mixture was 0.14 mg KOH/g sample. Volatiles were removed from the reaction mixture by heating at 60°C. under 300 mm Hg. absolute for 2 hours. There was obtained 483 grams of a clear colorless liquid. The acid number of the clear colorless liquid was less than 0.01 mg/KOH/g sample.

Analysis showed a phosphorus content equal to about 8.33 percent.

Having set forth the general nature and examples of the present invention, the scope is now particularly set forth in the appended claims.

What is claimed is:

1. A method of preparing compounds of the structural formula:

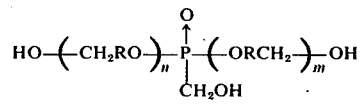

wherein R is $CH_2$,

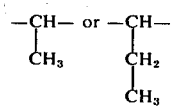

and $n+m = 2-10$; comprising the steps of:
a. contacting phosphorous acid with a reactant selected from the group consisting of formaldehyde and formaldehyde polymers at a temperature between about 90°C. and 150°C. to form an intermediate compound of the structural formula:

b. contacting said intermediate compound with an alkylene oxide selected from the group consisting of ethylene oxide, propylene oxide or butylene oxide at a temperature between about 30°C. and 100°C. to form a compound of structural formula (I).

2. The method of claim 1 wherein ethylene oxide and said intermediate compound are contacted by agitating said intermediate compound while adding gaseous ethylene oxide.

3. The method of claim 1 wherein said formaldehyde polymer is trioxane.

4. The method of claim 1 wherein said formaldehyde polymer is paraformaldehyde.

5. A method of preparing compounds of the structural formula:

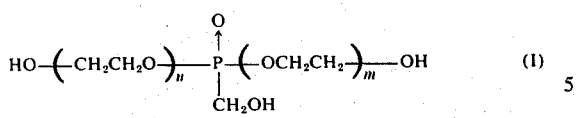 (I)

wherein $n + m = 2-10$; comprising the steps of:
a. contacting phosphorous acid with a reactant selected from the group consisting of formaldehyde and formaldehyde polymers in an aqueous medium at a temperature between about 90°C. and 150°C. followed by removing water and unreacted formaldehyde or formaldehyde polymers at a temperature between about 50°C. and 125°C. and a pressure between about 10 mm Hg. and 760 mm Hg. to form an intermediate compound of the structural formula:

 II b. contacting said intermediate compound with ethylene oxide by agitating said intermediate compound while adding gaseous ethylene oxide at a temperature between about 30°C. and 100°C. to form a compound of structural formula (I).

6. The method of claim 5 wherein said formaldehyde polymer is trioxane.

7. The method of claim 5 wherein said formaldehyde polymer is paraformaldehyde.

* * * * *